United States Patent [19]

Ogura et al.

[11] Patent Number: 5,752,920
[45] Date of Patent: May 19, 1998

[54] BLOOD PRESSURE MONITOR APPARATUS

[75] Inventors: Toshihiko Ogura, Inuyama; Hidekatsu Inukai, Nagoya, both of Japan

[73] Assignee: Colin Corporation, Komaki, Japan

[21] Appl. No.: 848,567

[22] Filed: Apr. 28, 1997

[30] Foreign Application Priority Data

Aug. 1, 1996 [JP] Japan ................................. 8-203837
Aug. 1, 1996 [JP] Japan ................................. 8-203838

[51] Int. Cl.$^6$ ................................................ A61B 5/00
[52] U.S. Cl. ......................... 600/494; 600/495; 600/485; 600/500
[58] Field of Search .................... 600/485, 490, 600/493–496, 500, 561

[56] References Cited

U.S. PATENT DOCUMENTS

| | | | |
|---|---|---|---|
| 560,329 | 2/1896 | Hosaka et al. | 600/493 |
| 4,807,638 | 2/1989 | Sramek | 600/485 |
| 4,907,596 | 3/1990 | Schmid et al. | 600/485 |
| 5,131,391 | 7/1992 | Sakai et al. | |
| 5,237,997 | 8/1993 | Greubel et al. | 600/485 |
| 5,564,427 | 10/1996 | Aso et al. | 400/494 |
| 5,649,543 | 7/1997 | Hosaka et al. | 600/493 |

Primary Examiner—Robert L. Nasser
Attorney, Agent, or Firm—Oliff & Berridge, PLC

[57] ABSTRACT

A blood pressure monitor apparatus including a blood pressure measuring device which includes a cuff and measures a blood pressure value of a living subject by changing a pressing pressure of the cuff applied to a body portion of the subject, an estimated blood pressure determining device for successively determining an estimated blood pressure value of the subject, based on each of successive sets of actual pulse-wave propagation information, according to a predetermined relationship between blood pressure and pulse-wave propagation information, a pulse period measuring device which successively measures a period of a pulse of the subject, a peripheral pulse wave detecting device which detects a peripheral pulse wave from a peripheral body portion of the subject, a pulse-wave area calculating device for successively calculating an area defined by a waveform of a pulse of the peripheral pulse wave detected by the peripheral pulse wave detecting device, and a blood pressure measurement starting device for starting a blood pressure measurement of the blood pressure measuring device, when an amount of change of the estimated blood pressure values is greater than a first reference value and at least one of an amount of change of the measured pulse periods and an amount of change of the calculated pulse-wave areas is greater than a corresponding one of a second and a third reference value.

15 Claims, 10 Drawing Sheets

BLOOD PRESSURE MONITOR APPARATUS

BACKGROUND OF THE INVENTION

1. Field of the Invention

The present invention relates to a blood pressure monitor apparatus which monitors a blood pressure of a living subject, based on information on a pulse wave which propagates through an artery of the subject.

2. Related Art Statement

There is known, as information on a pulse wave which propagates through an artery of a living subject, a pulse-wave propagation time DT or a pulse-wave propagation velocity $V_M$ (m/s). The pulse-wave propagation time DT represents a time in which a pulse wave propagates between predetermined two different locations of the subject. Additionally, there is known that the pulse-wave propagation information is, within a predetermined range, substantially proportional to a blood pressure BP (mmHg) of the subject. Therefore, there has been proposed a blood pressure monitor apparatus which determines, in advance, coefficients $\alpha$, $\beta$ in an expression: $EBP = \alpha(DT) + \beta$ (where $\alpha$ is a negative value) or $EBP = \alpha(V_M) + \beta$ (where $\alpha$ is a positive value), based on a measured blood pressure value BP of the subject and an obtained pulse-wave propagation time (DT) or an obtained pulse-wave propagation velocity ($V_M$), determines an estimated blood pressure value EBP of the subject, based on each set of subsequently obtained pulse-wave propagation information, according to the above mentioned expression, and starts a blood pressure measurement using a cuff upon detection of abnormality of the estimated blood pressure value EBP.

However, for the purpose of improving the reliability of the estimated-blood-pressure abnormality judgment, the above described blood pressure monitor apparatus employs a large reference range for finding an abnormality of the estimated blood pressure value EBP, because the relationship between the blood pressure and the pulse-wave propagation information changes due to the conditions of a central organ of the subject (e.g., conditions of cardiac muscle), and/or the conditions of a peripheral organ of the subject (e.g., hardness of blood vessels and/or resistance of the same to blood flow). Therefore, in the blood pressure monitor apparatus, the starting of blood pressure measuring operation may be delayed in spite of occurrence of abrupt blood pressure change or the like, so that the accuracy of operation of the blood pressure monitor is deteriorated.

SUMMERY OF THE INVENTION

It is therefore an object of the present invention to provide a blood pressure monitor apparatus which monitors, with high accuracy, a blood pressure of a living subject, based on information on a pulse wave which propagates through an artery of the subject.

The above object has been achieved by the present invention. According to a first aspect of the present invention, there is provided a blood pressure monitor apparatus comprising: (a) a blood pressure measuring device which includes a cuff and measures a blood pressure value of a living subject by changing a pressing pressure of the cuff applied to a body portion of the subject; (b) estimated blood pressure determining means for successively determining an estimated blood pressure value of the subject, based on each of successive sets of actual pulse-wave propagation information, according to a predetermined relationship between blood pressure and pulse-wave propagation information; (c) a pulse period measuring device which successively measures a period of a pulse of the subject; (d) a peripheral pulse wave detecting device which detects a peripheral pulse wave from a peripheral body portion of the subject; (e) pulse-wave area calculating means for successively calculating an area defined by a waveform of a pulse of the peripheral pulse wave detected by the peripheral pulse wave detecting device; and (f) blood pressure measurement starting means for starting a blood pressure measurement of the blood pressure measuring device, when an amount of change of the estimated blood pressure values is greater than a first reference value and at least one of an amount of change of the measured pulse periods and an amount of change of the calculated pulse-wave areas is greater than a corresponding one of a second and a third reference value. The inventors of the present invention have continued their study in the background of the above described situation, and they have found that, when either one of the pulse period obtained as information on the central organ of subject's circulatory system and the pulse-wave area obtained as information on the peripheral organ of the circulatory system is employed as a criterion of the estimated-blood-pressure abnormality judgment, it is possible to improve greatly the reliability of blood-pressure abnormality judgment.

In the blood pressure monitor apparatus in accordance with the first aspect of the present invention, the blood pressure measurement starting means starts a blood pressure measurement of the blood pressure measuring device, when an amount of change of the estimated blood pressure values determined by the estimated blood pressure determining means is greater than the first reference value and at least one of an amount of change of the measured pulse periods and an amount of change of the calculated pulse-wave areas is greater than a corresponding one of the second and the third reference value. Thus, the present blood pressure monitor apparatus can employ as small as possible reference values for finding abnormalities and accordingly identify, without any delay, abrupt blood pressure changes, in comparison with a conventional blood pressure monitor apparatus which starts a blood pressure measuring operation, based on only the judgment of abnormality of estimated blood pressure values. The reliability of the present blood pressure monitor apparatus is thus improved.

According to a preferred feature of the first aspect of the invention, the blood pressure monitor apparatus further comprises pulse-wave propagation information obtaining means for obtaining the each set of pulse-wave propagation information.

According to another feature of the first aspect of the invention, the blood pressure monitor apparatus further comprises blood pressure-pulse wave propagation information relationship determining means for determining the relationship between blood pressure and pulse-wave propagation information, based on a blood pressure value measured by the blood pressure measuring device and a set of pulse-wave propagation information obtained by the pulse-wave propagation information obtaining means.

According to another feature of the first aspect of the invention, the pulse-wave propagation information obtaining means comprises means for calculating, as the each set of pulse-wave propagation information, at least one of a propagation time and a propagation velocity, based on a time difference between a predetermined point of an electrocardiographic waveform and a predetermined point of a waveform of a pressure pulse wave or a volume pulse wave detected from the peripheral body portion of the subject. In this particular case, the present monitor apparatus can obtain a large time difference in comparison with that obtained in the case where two pressure pulse wave sensors are set on different locations above on an artery of the subject. Thus, the accuracy of the pulse-wave propagation time and/or the pulse-wave propagation velocity improves.

According to another feature of the first aspect of the invention, the blood pressure monitor apparatus further comprises an electrocardiographic waveform detecting device which includes a plurality of electrodes adapted to be put on a body surface of the subject and detects an electrocardiographic waveform through the electrodes. In this case, the pulse period measuring device may measure, as a pulse period, a time difference between respective predetermined points (e.g., R-waves) of successive two pulses of the electrocardiographic waveform detected by the electrocardiographic waveform detecting device.

According to another feature of the first aspect of the invention, the peripheral pulse wave detecting device comprises a photoelectric pulse wave sensor including a light-emitting and a light-receiving element, the light-emitting element emitting, toward a body surface of the subject, a light including a wavelength which can be reflected by hemoglobin present in blood of the subject, the light-receiving element receiving the light scattered by the hemoglobin from the body surface of the subject. In this case, the present apparatus can easily obtain a photoelectric pulse wave representative of the pulse-synchronous change of blood volume, that is, a volume pulse wave.

According to another feature of the first aspect of the invention, the pulse-wave area calculating means comprises means for calculating the pulse-wave area which is normalized based on a period and an amplitude of the pulse of the peripheral pulse wave. In this case, the blood pressure monitor apparatus can obtain a pulse-wave area value free from timewise changes or individual differences.

According to another feature of the first aspect of the invention, the blood pressure monitor apparatus further comprises a display device which concurrently displays respective trend graphs of the estimated blood pressure values successively determined by the estimated blood pressure determining means, the pulse period values successively measured by the pulse period measuring device and the pulse-wave area values successively calculated by the pulse-wave area calculating means. Since the three trend graphs are concurrently displayed on the display device, it is possible for a medical person to ascertain the reason of the starting of the blood pressure measurement by the blood pressure measurement starting means and to easily monitor the dynamic condition of the circulatory organ of the subject while the blood pressure measurements of the blood pressure measuring device are not carried out.

According to a second aspect of the present invention, there is provided a blood pressure monitor apparatus comprising: (a) a blood pressure measuring device which includes a cuff and measures a blood pressure value of a living subject by changing a pressing pressure of the cuff applied to a body portion of the subject; (b) estimated blood pressure determining means for successively determining an estimated blood pressure value of the subject, based on each of successive sets of actual pulse-wave propagation information, according to a predetermined relationship between blood pressure and pulse-wave propagation information; (g) a heart rate measuring device which measures a heart rate of the subject; and (f) relationship correcting means for correcting the predetermined relationship between blood pressure and pulse-wave propagation information, based on the heart rate measured by the heart rate measuring device. The present inventors have found that, when the relationship between blood pressure and pulse-wave propagation information is corrected by utilizing the heart rate obtained as information on the central organ of the circulatory system, it is possible to improve greatly the reliability of the blood pressure monitor apparatus.

In the blood pressure monitor apparatus in accordance with the second aspect of the invention, the relationship correcting means corrects the predetermined relationship between blood pressure and pulse-wave propagation information, based on the heart rate measured by the heart rate measuring device. Therefore, the accuracy of the estimated blood pressure values is improved, whereby the reliability of the blood pressure monitor increases.

According to a preferred feature of the second aspect of the invention, the predetermined relationship comprises a relationship between estimated blood pressure (EBP) and pulse-wave propagation time (DT) which is represented by an expression: $EBP=\alpha DT+\beta$, and the relationship correcting means corrects the expression by decreasing an absolute value of the negative coefficient a for the pulse-wave propagation time DT, with the increasing of the heart rate.

According to another feature of the second aspect of the invention, the predetermined relationship comprises a relationship between estimated blood pressure (EBP) and pulse-wave propagation velocity ($V_M$) which is represented by an expression: $EBP=\alpha V_M+\beta$, and the relationship correcting means corrects the expression by increasing an absolute value of the positive coefficient $\alpha$ for the pulse-wave propagation velocity $V_M$, with the increasing of the heart rate.

In each of the above two cases, the relationship correcting means corrects the relationship so that the estimated blood pressure value increases with the increasing of the heart rate HR, whereby the accuracy of the estimated blood pressures and the reliability of the blood pressure monitor are raised.

According to another feature of the second aspect of the invention, the blood pressure monitor apparatus further comprising: (c) a pulse period measuring device which successively measures a period of a pulse of the subject; (d) a peripheral pulse wave detecting device which detects a peripheral pulse wave from the peripheral body portion of the subject; (e) pulse-wave area calculating means for successively calculating an area defined by a waveform of a pulse of the peripheral pulse wave detected by the peripheral pulse wave detecting device; and (f) blood pressure measurement starting means for starting a blood pressure measurement of the blood pressure measuring device, when an amount of change of the estimated blood pressure values is greater than a first reference value and at least one of an amount of change of the measured pulse periods and an amount of change of the calculated pulse-wave areas is greater than a corresponding one of a second and a third reference value.

BRIEF DESCRIPTION OF THE DRAWINGS

The above and optional objects, features, and advantages of the present invention will better be understood by reading the following detailed description of the preferred embodiments of the invention when considered in conjunction with the accompanying drawings, in which.

DETAILED DESCRIPTION OF THE PREFERRED EMBODIMENTS

Figure 1:
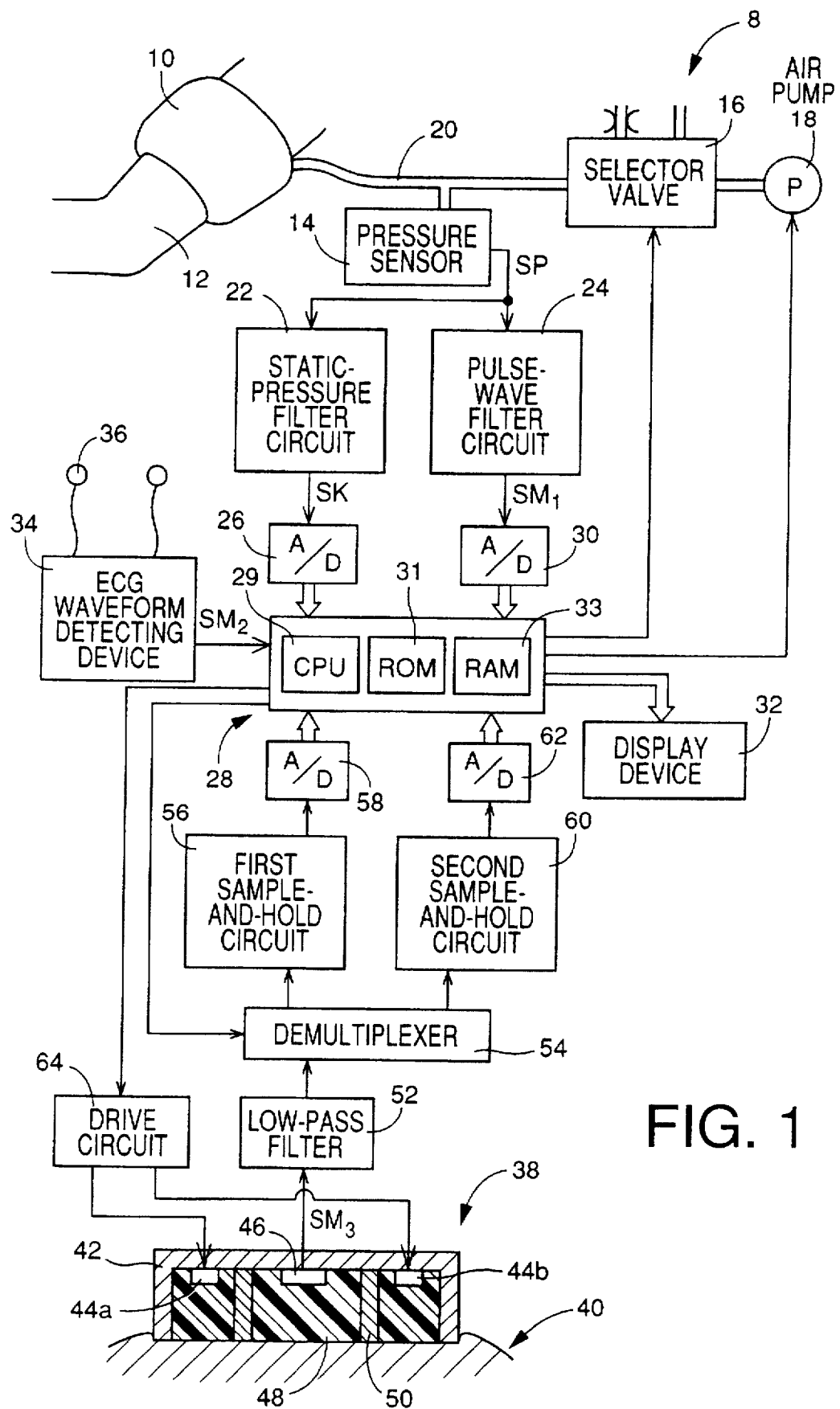
FIG. 1 is a diagrammatic view of a blood pressure monitor apparatus embodying the present invention.

Referring to FIG. 1, there will be described a blood pressure (BP) monitor apparatus 8 embodying the present invention.

In FIG. 1, the BP monitor apparatus 8 includes a cuff 10 which has a belt-like cloth bag and a rubber bag accommodated in the cloth bag and which is adapted to be wound around an upper arm 12 of a patient, for example, a pressure sensor 14, a selector valve 16 and an air pump 18 each of which is connected to the cuff 10 via a piping 20. The selector valve 16 is selectively placed in an inflation position in which the selector valve 16 permits a pressurized air to be supplied to the cuff 10, a slow-deflation position in which the selector valve 16 permits the pressurized air to be slowly discharged from the cuff 10, and a quick-deflation position in which the selector valve 16 permits the pressurized air to be quickly discharged from the cuff 10.

The pressure sensor 14 detects an air pressure in the cuff 10, and supplies a pressure signal SP representative of the detected pressure to each of a static pressure filter circuit 22 and a pulse-wave filter circuit 24. The static pressure filter circuit 22 includes a low-pass filter and extracts, from the pressure signal SP, a static component contained in the pressure signal SP, i.e., cuff pressure signal SK representative of the static cuff pressure. The cuff pressure signal SK is supplied to an electronic control device 28 via an analog-to-digital (A/D) converter 26. The pulse-wave filter circuit 24 includes a band-pass filter and extracts, from the pressure signal SP, an oscillating component having predetermined frequencies, i.e., pulse-wave signal $SM_1$. The pulse-wave signal $SM_1$ is supplied to the electronic control device 28 via an A/D converter 30. The pulse-wave signal $SM_1$ represents an oscillatory pressure wave which is produced from a brachial artery (not shown) of the patient in synchronism with the heartbeat of the patient and is propagated to the cuff 10.

The electronic control device 28 is provided by a so-called microcomputer including a central processing unit (CPU) 29, a read only memory (ROM) 31, a random access memory (RAM) 33 and an input-and-output (I/O) port (not shown). The CPU 29 processes signals according to control programs pre-stored in the ROM 31 by utilizing a temporary-storage function of the RAM 33, and supplies drive signals to the selector valve 16 and the air pump 18 through the I/O port.

The BP monitor apparatus 8 further includes an electrocardiographic (ECG) waveform detecting device 34 which continuously detects an ECG waveform representative of an action potential of a cardiac muscle of a living subject, through a plurality of electrodes 36 being put on predetermined portions of the subject, and supplies an ECG waveform signal $SM_2$ representative of the detected ECG waveform to the electronic control device 28. The ECG waveform detecting device 34 is used for detecting a Q-wave or a R-wave of the ECG waveform which corresponds to a time point when the output of blood from the heart of the subject toward the aorta of the subject is started. Thus, the ECG waveform detecting device 34 functions as a first pulse wave detecting device.

The BP monitor apparatus 8 still further includes a photoelectric pulse wave detecting probe 38 (hereinafter, referred to as the "probe") which is employed as part of a pulse oximeter. The probe 38 may function as a second pulse wave detecting device or a peripheral pulse wave detecting device for detecting a pulse wave propagated to a peripheral artery including capillaries. The probe 38 is adapted to be set on a skin or a body surface 40 of the subject, e.g., an end portion of a finger of the patient, with the help of a band (not shown) such that the probe 38 closely contacts the body surface 40. The probe 38 includes a container-like housing 42 which opens in a certain direction, a first and a second group of light emitting elements 44a, 44b, such as LEDs (light emitting diodes), which are disposed on an outer peripheral portion of an inner bottom surface of the housing 42 (hereinafter, referred to as the light emitting elements 44 in the case where the first and second group of light emitting elements 44a, 44b need not be discriminated from each other), a light receiving element 46, such as a photodiode or a phototransister, which is disposed on a central portion of the inner bottom surface of the housing 42, a transparent resin 48 which is integrally disposed in the housing 42 to cover the light emitting elements 44 and the light receiving element 46, and an annular shade member 50 which is disposed between the light emitting elements 44 and the light receiving element 46, for preventing the lights emitted toward the body surface 40 by the light emitting elements 44 and reflected from the body surface 40, from being received by the light receiving element 46.

The first and second groups of light emitting elements 44a, 44b emit a red light having about 660 nm wavelength and an infrared light having about 800 nm wavelength, respectively. The first and second light emitting elements 44a, 44b alternately emit the red and infrared lights at a predetermined frequency. The lights emitted toward the body surface 40 by the light emitting elements 44 are reflected from a body tissue of the subject where a dense capillaries occur, and the reflected lights are received by the common light receiving element 46. In place of the 660 nm and 800 nm wavelengths lights. the first and second light emitting elements 44a, 44b may employ various pairs of lights each pair of which have different wavelengths, so long as one light of each pair exhibits significantly different absorption factors with respect to oxygenated hemoglobin and reduced hemoglobin, respectively, and the other light exhibits substantially same absorption factors with respect to the two sorts of hemoglobin, i.e., has a wavelength which is reflected by each of the two sorts of hemoglobin.

The light receiving element 46 outputs, through a low-pass filter 52, a photoelectric pulse-wave signal $SM_3$ representative of an amount of the received light. The light receiving element 46 is connected to the low-pass filter 52 via an amplifier or the like. The low-pass filter 52 eliminates, from the photoelectric pulse-wave signal $SM_3$ input thereto, noise having frequencies higher than that of a pulse wave, and outputs the noise-free signal $SM_3$, to a demultiplexer 54. The photoelectric pulse wave represented by the photoelectric pulse-wave signal $SM_3$ can be said as a volume pulse wave produced in synchronism with a pulse of the patient. That is, the photoelectric pulse wave is a pulse-synchronous wave.

The demultiplexer 54 is alternately switched according to signals supplied thereto from the electronic control device 28 in synchronism with the light emissions of the first and second light emitting elements 44a, 44b. Thus, the demultiplexer 54 successively supplies, to the I/O port (not shown) of the electronic control device 28, an electric signal $SM_R$ representative of the red light through a first sample-and-hold circuit 56 and an A/D converter 58, and an electric signal $SM_{IR}$ representative of the infrared light through a second sample-and-hold circuit 60 and an A/D converter 62. The first and second sample-and-hold circuits 56, 60 hold the electric signals $SM_R$, $SM_{IR}$ input thereto, respectively, and do not output those current signals to the A/D converters 58, 62, before the prior signals $SM_R$, $SM_{IR}$ are completely converted by the two A/D converters 58, 62, respectively.

In the electronic control device 28, the CPU 29 carries out a measuring operation according to control programs pre-stored in the ROM 31 by utilizing a temporary-storage function of the RAM 33. More specifically, the CPU 29 generates a light emit signal SLV to a drive circuit 64 so that the first and second light emitting elements 44a, 44b alternately emit the red and infrared lights at a predetermined frequency, respectively, such that each light emission lasts for a predetermined period. In synchronism with the alternate light emissions by the first and second light emitting elements 44a, 44b, the CPU 29 generates a switch signal SC to the demultiplexer 54 so as to correspondingly place the demultiplexer 54 in a first or a second position. Thus, the signals $SM_R$, $SM_{IR}$ are separated from each other by the demultiplexer 54 such that the signal $SM_R$ is supplied to the first sample-and-hold circuit 56 while the signal $SM_{IR}$ is supplied to the second sample-and-hold circuit 60. Further, the CPU 29 determines an oxygen saturation in the blood of the subject, based on respective amplitudes of the signals $SM_R$, $SM_{IR}$, according to a predetermined expression pre-stored in the ROM 31. The blood oxygen saturation determining method is disclosed in U.S. Pat. No. 5,131,391.

Figure 2:
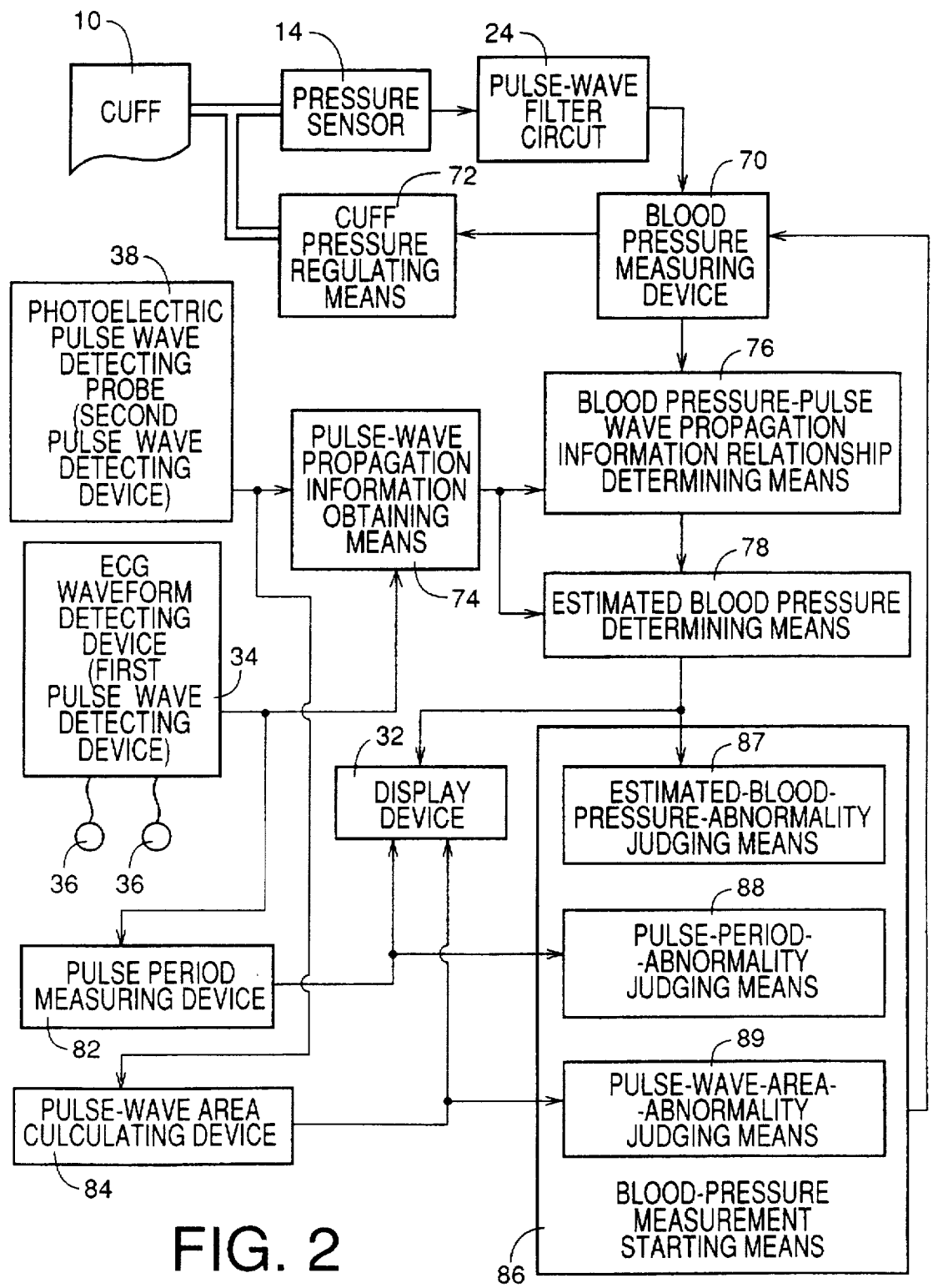
FIG. 2 is a block diagram for illustrating essential functions of an electronic control device 28 of the apparatus of FIG. 1.

FIG. 2 illustrates essential functions of the electronic control device 28 of the present BP monitor apparatus 8. In the figure, a blood pressure measuring device 70 measures a systolic, a mean and a diastolic blood pressure value $BP_{SYS}$, $BP_{MEAN}$, $BP_{DIA}$, of the subject, according to a well-known oscillometric method, based on variation of respective magnitudes of pulses of the pulse wave represented by the pulse-wave signal $SM_1$ obtained while the cuff pressure which is quickly increased, by a cuff pressure regulating means 72, to a target value $P_{CM}$ (e.g., 180 mmHg), is slowly decreased at the rate of about 3 mmHg/sec.

Figure 3:
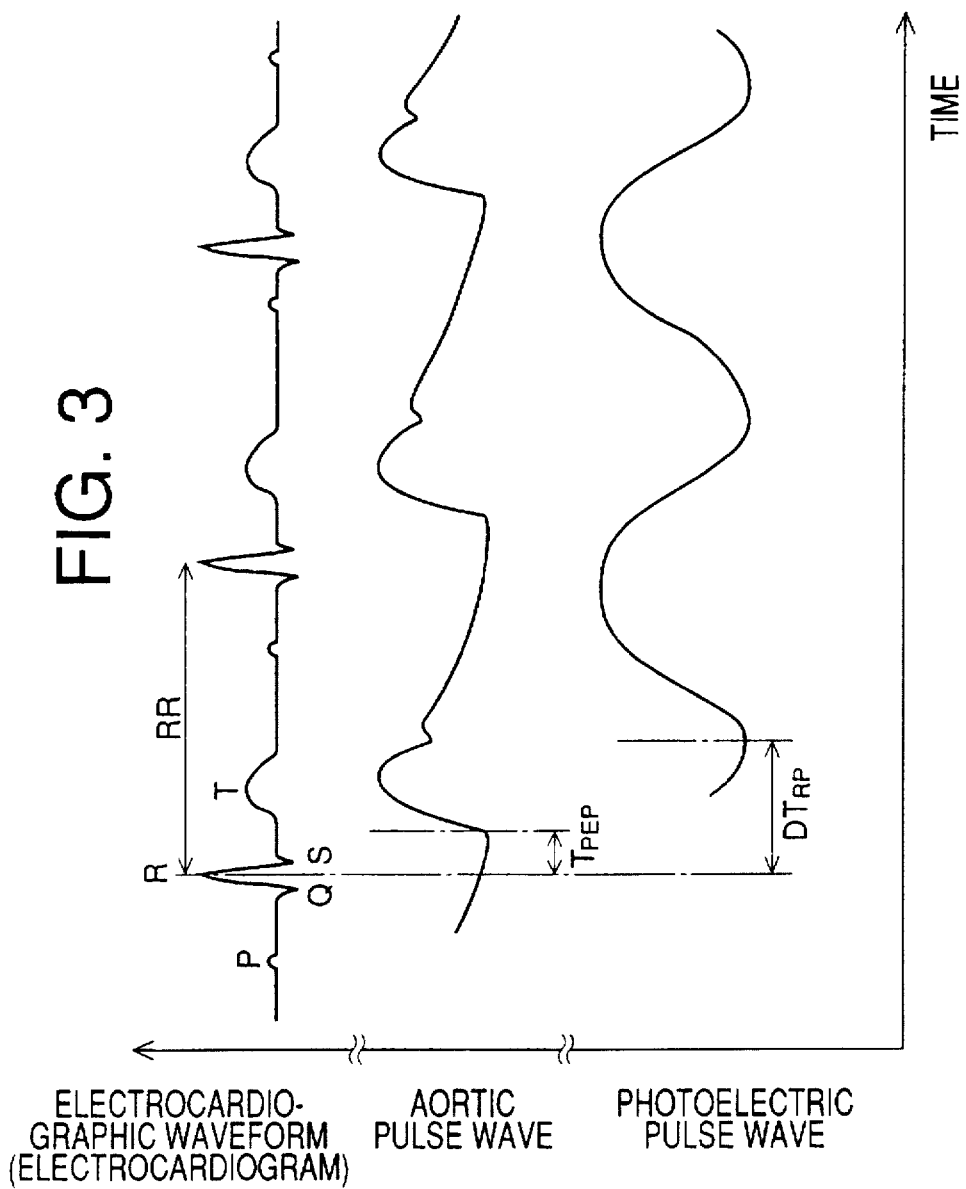
FIG. 3 is a view to show a time difference $DT_{RP}$ obtained by the operation of the electronic control device 28.

A pulse-wave propagation information obtaining means 74 includes a time-difference calculating means for calculating, as a pulse-wave propagation time $DT_{RP}$, a time difference between a predetermined point (e.g., R-wave) of the ECG waveform of each of periodic pulses successively detected by the ECG waveform detecting device 34 and a predetermined point (e.g., rising point or minimum point) of the waveform of a corresponding one of periodic pulses of the photoelectric pulse wave detected by the probe 38, as shown in FIG. 3. The pulse-wave propagation information obtaining means 74 further calculates a pulse-wave propagation velocity $V_M$ (m/sec) of the pulse wave propagated through the artery of the patient, based on the calculated pulse-wave propagation time $DT_{RP}$, according to the following expression (1) pre-stored in the ROM 31:

$$V_M = L/(DT_{RP} - T_{PEP}) \tag{1}$$

where L (m) is a length of the artery as measured from the left ventricle to the position at which the probe 38 is set, via the aorta; and $T^{PEP}$ (sec) is a pre-ejection period between the R-wave of the ECG waveform of each pulse and the minimum point of the waveform of a corresponding pulse of the photoelectric pulse wave. The values L and $T_{PEP}$ are constants, respectively, and are experimentally obtained in advance.

A blood pressure-pulse wave propagation information relationship determining means 76 determines, in advance, two coefficients α, β in the following expressions (2) and (3), based on the systolic blood pressure value $BP_{SYS}$ measured by the blood pressure measuring device 70 and either one of the pulse-wave propagation time $DT_{RP}$ and the pulse-wave propagation velocity $V_M$ (e.g., either one of respective average values of the pulse-wave propagation time values $DT_{RP}$ and the pulse-wave propagation velocity values $V_M$ obtained during each blood pressure measurement). The expressions (2) and (3) respectively show a relationship between systolic blood pressure $BP_{SYS}$ and pulse-wave propagation time $DT_{RP}$, and a relationship between systolic blood pressure $BP_{SYS}$ and pulse-wave propagation velocity $V_M$. In place of the relationship between systolic blood pressure $BP_{SYS}$ and either one of the pulse-wave propagation time $DT_{RP}$ and the pulse-wave velocity $V_M$, a relationship between a mean or a diastolic blood pressure measured by the blood pressure measuring device 70 and either one of the pulse-wave propagation time $DT_{RP}$ and the pulse-wave velocity $V_M$ may be employed. In short, the blood pressure-pulse wave propagation information relationship may be determined depending upon which one of the systolic, mean and diastolic blood pressure value is selected as a monitor (estimated) blood pressure value EBP.

$$EBP = \alpha(DT_{RP}) + \beta \tag{2}$$

where α is a negative constant and β is a positive constant.

$$EBP = \alpha(V_M) + \beta \tag{3}$$

where α is a positive constant and β is a positive constant.

Figure 4:
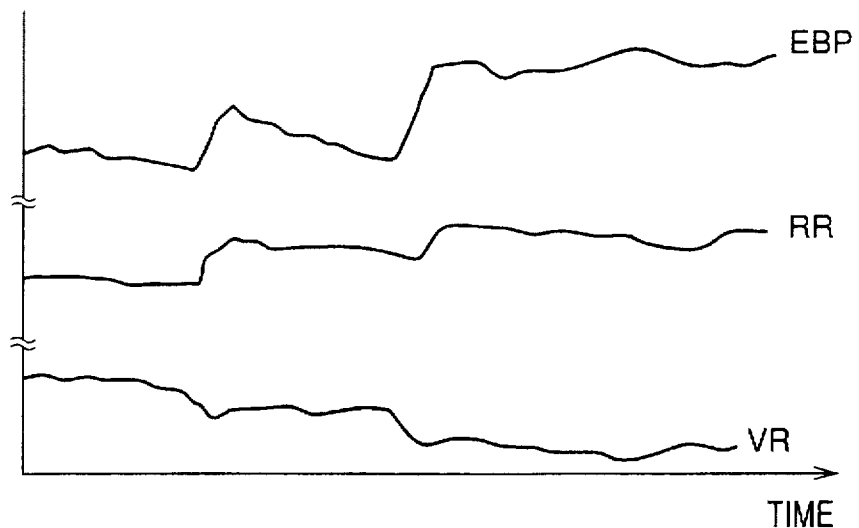
FIG. 4 is a view to show respective trend graphs of estimated blood pressure values EBP, pulse period values RR and pulse-wave area values VR obtained on the apparatus of FIG. 1, which are concurrently displayed on a display device.

An estimated blood pressure determining means 78 successively determines the estimated blood pressure value EBP of the subject, based on either one of the actual pulse-wave propagation time $DT_{RP}$ and pulse-wave propagation velocity $V_M$ successively obtained by the pulse-wave propagation information obtaining means 74, according to the blood pressure-pulse wave propagation information relationship (represented by the expression (2) or (3)). The control device 28 controls a display device 32 to concurrently display the thus determined estimated blood pressure values EBP together with pulse period values RR and pulse-wave area values VR (which will be described below) in respective trend graphs along the common axis representative of time, as shown in FIG. 4.

Figure 5:
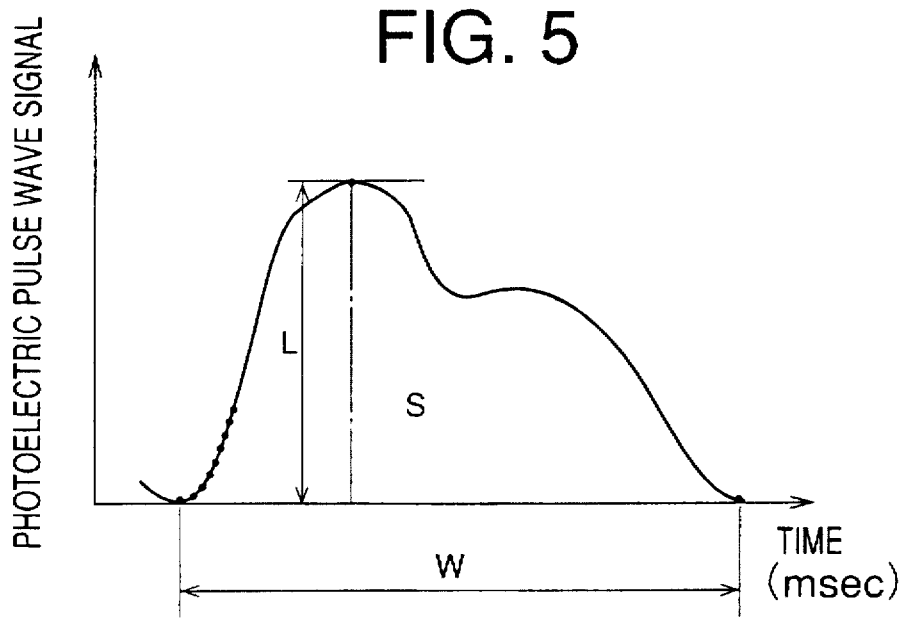
FIG. 5 is a view for explaining a normalization of the pulse-wave area VR.

A pulse period measuring device 82 measures a pulse period RR by measuring a time difference between respective predetermined points (e.g., R-waves) of successive two pulses of the ECG waveform detected by the ECG waveform detecting device 34. A pulse-wave area calculating means 84 calculates a pulse-wave area VR by normalizing an area S defined by a waveform of each pulse of the photoelectric pulse wave which is detected by the probe 38, based on a period W and an amplitude L of the pulse of the photoelectric pulse wave. More specifically, as shown in FIG. 5, the waveform of each pulse of the photoelectric pulse wave is defined by a series of data points indicative of respective magnitudes which are input at a predetermined interval such as several milliseconds to several tens of milliseconds. The pulse-wave area S is obtained by integrating, in the period W of the pulse of the photoelectric pulse wave, the respective magnitudes of the pulse of the photoelectric pulse wave being input at the predetermined interval, and then the normalized pulse-wave area VR is obtained by calculating the following expression: $VR = S/(W \times L)$. The normalized pulse-wave area VR is a dimensionless value indicative of a ratio of the pulse-wave area to an area defined by the period W and the amplitude L of each pulse of the photoelectric pulse wave. In other cases, a symbol %MAP may be used in place of the symbol VR.

A blood-pressure measurement starting means 86 starts a blood-pressure measurement of the blood pressure measuring device 70, when an amount of change of the estimated blood pressure value EBP is greater than a first reference value and at least one of an amount of change of the measured pulse period RR and an amount of change of the calculated pulse-wave area VR is greater than a corresponding one of a second and a third reference value. For instance, the blood-pressure measurement starting means 86 includes an estimated-blood-pressure-abnormality judging means 87 for judging that an estimated blood pressure EBP determined by the estimated blood pressure determining means 78 is abnormal when the estimated blood pressure value EBP is, by not less than a predetermined first value or a predetermined first ratio, greater or smaller than an actual blood pressure value determined in the prior blood pressure measurement using the cuff 10, a pulse-period-abnormality judging means 88 for judging that a pulse period RR measured by the pulse period measuring device 82 is abnormal when the pulse period RR is, by not less than a predetermined second value or a predetermined second ratio, greater or smaller than a pulse period measured in the prior blood pressure measurement using the cuff 10, and a pulse-wave-area-abnormality judging means 89 for judging that a pulse-wave area VR calculated by the pulse-wave area calculating means 84 is abnormal when the pulse-wave area VR is, by not less than a predetermined third value or a predetermined third ratio, greater or smaller than a pulse-wave area calculated in the prior blood pressure measurement using the cuff 10. Each of the first, second, and third ratios is predetermined based on a corresponding one of the blood pressure value, pulse period, and pulse-wave area obtained in the prior blood pressure measurement. Thus, when the estimated-blood-pressure-abnormality judging means 87 judges that an estimated blood-pressure value EBP is abnormal and at least one of the pulse-period-abnormality judging means 88 and the pulse-wave-area-abnormality judging means 89 judges that a corresponding one of a pulse period RR and a pulse-wave area VR is abnormal, the blood-pressure measurement starting means 86 starts a blood-pressure measurement of the blood pressure measuring device 70.

Next, there will be described the operation of the control device 28 of the BP monitor apparatus 8 by reference to the flow charts of FIGS. 6 and 7.

Figure 6:
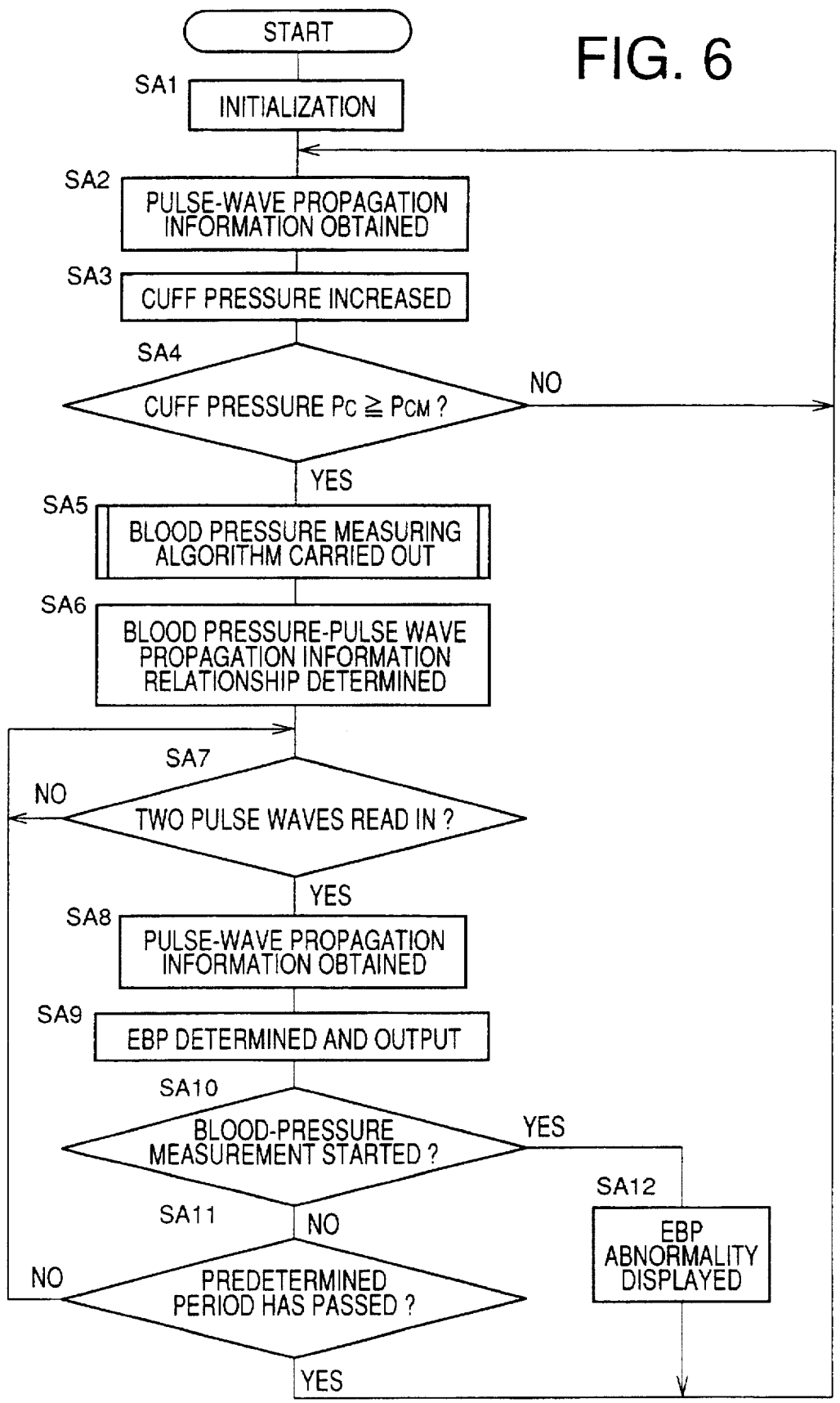
FIG. 6 is a flow chart representing a control program according to which the apparatus of FIG. 1 is operated.

The control of the CPU 29 begins with Step SA1 of the flow chart of FIG. 6, where flags, a counter and a register (which are not shown) are reset. Step SA1 is followed by Step SA2 to calculate, as a pulse-wave propagation time $DT_{RP}$, a time difference between a R-wave of the ECG waveform of a pulse and a rising point of the waveform of a corresponding pulse of the photoelectric pulse wave obtained before the increasing of the cuff pressure, and then calculate a pulse-wave propagation velocity $V_M$ (m/sec) based on the calculated pulse-wave propagation time $DT_{RP}$ according to the expression (1) before the increasing of the cuff pressure. Step SA2 corresponds to the pulse-wave propagation information obtaining means 74.

The control of the CPU 29 goes to Steps SA3 and SA4 corresponding to the cuff pressure regulating means 72. At Step SA3, the CPU 29 starts to quickly increase the cuff pressure for a blood pressure measurement, by switching the selector valve 16 to the inflation position and operating the air pump 18. Step SA3 is followed by Step SA4 to judge whether or not the cuff pressure $P_C$ is equal to or greater than a predetermined target value $P_{CM}$ (e.g., 180 mmHg). If a negative judgement is made at Step SA4, the control of the CPU 29 goes back to Step SA2 so as to continue to increase the cuff pressure $P_C$.

If a positive judgement is made at Step SA4, the control of the CPU 29 goes to Step SA5 to carry out a blood pressure measuring algorithm. More specifically, the air pump 18 is stopped and the selector value 16 is switched to the slow-deflation position where the selector valve 16 permits the pressurized air to be slowly discharged from the cuff 10. A systolic blood pressure value $BP_{SYS}$, a mean blood pressure value $BP_{MEAN}$ and a diastolic blood pressure value $BP_{DIA}$ are determined, according to a well known oscillometric type blood pressure determining algorithm, based on the variation of respective amplitudes of pulses of the pulse wave represented by the pulse wave signal $SM_1$ obtained while the cuff pressure is slowly decreased at a predetermined rate of about 3 mmHg/sec, and a pulse rate is determined based on the interval of successive two pulses of the pulse wave. The thus measured blood pressure values and pulse rate are displayed on the display device 32, and the selector valve 16 is switched to the quick-deflation position where the selector valve 16 permits the pressurized air to be quickly discharged from the cuff 10. Step SA5 corresponds to part of the blood pressure measuring device 70.

Next, Step SA5 is followed by Step SA6 to determine a blood pressure-pulse wave propagation information relationship between one of the blood pressure values $BP_{SYS}$, $BP_{MEAN}$, $BP_{DIA}$ measured at Step SA5 and one of the pulse-wave propagation time $DT_{RP}$ and the pulse-wave propagation velocity $V_M$ calculated at Step SA2. More specifically, when at Step SA5 the blood pressure values $BP_{SYS}$, $BP_{MEAN}$, $BP_{DIA}$ are measured, then at Step SA6 the relationship (the expression (2) or (3)) between estimated blood pressure EBP and one of the pulse-wave propagation time $DT_{RP}$ and the pulse-wave propagation velocity $V_M$ is determined, based on one of the blood pressure values $BP_{SYS}$, $BP_{MEAN}$, $BP_{DIA}$ and one of the pulse-wave propagation time $DT_{RP}$ and propagation velocity $V_M$. Step SA6 corresponds to the pulse wave propagation information-blood pressure relationship determining means 76.

Step SA6 is followed by Step SA7 to judge whether or not the R-wave of the ECG waveform of a pulse and the waveform of a corresponding pulse of the photoelectric pulse wave have been read in. If a negative judgment is made at Step SA7, the control of the CPU 29 waits until a positive judgment is made at Step SA7. If a positive judgment is made at Step SA7, the control of the CPU 29 goes to Step SA8 corresponding to the pulse-wave propagation information obtaining means 74. At Step SA8, the CPU 29 calculates a pulse-wave propagation time $DT_{RP}$ and a pulse-wave propagation velocity $V_M$ based on the R-wave of the ECG waveform and the waveform of the photoelectric pulse wave read in at Step SA7 in the same manner as carried out at Step SA2.

Step SA8 is followed by Step SA9 corresponding to the estimated blood pressure determining means 78. At Step SA9, the CPU 29 determines an estimated blood pressure value EBP (a systolic, a mean or a diastolic blood pressure value), based on one of the pulse-wave propagation time $DT_{RP}$ and the pulse-wave propagation velocity $V_M$ calculated at Step SA8, according to the blood pressure-pulse wave propagation information relationship determined at Step SA6. Further, the CPU 29 displays, on the display device 32, a trend graph of the estimated blood pressure values EBP determined for respective pulses of the ECG waveform and the photoelectric pulse wave.

Figure 7:
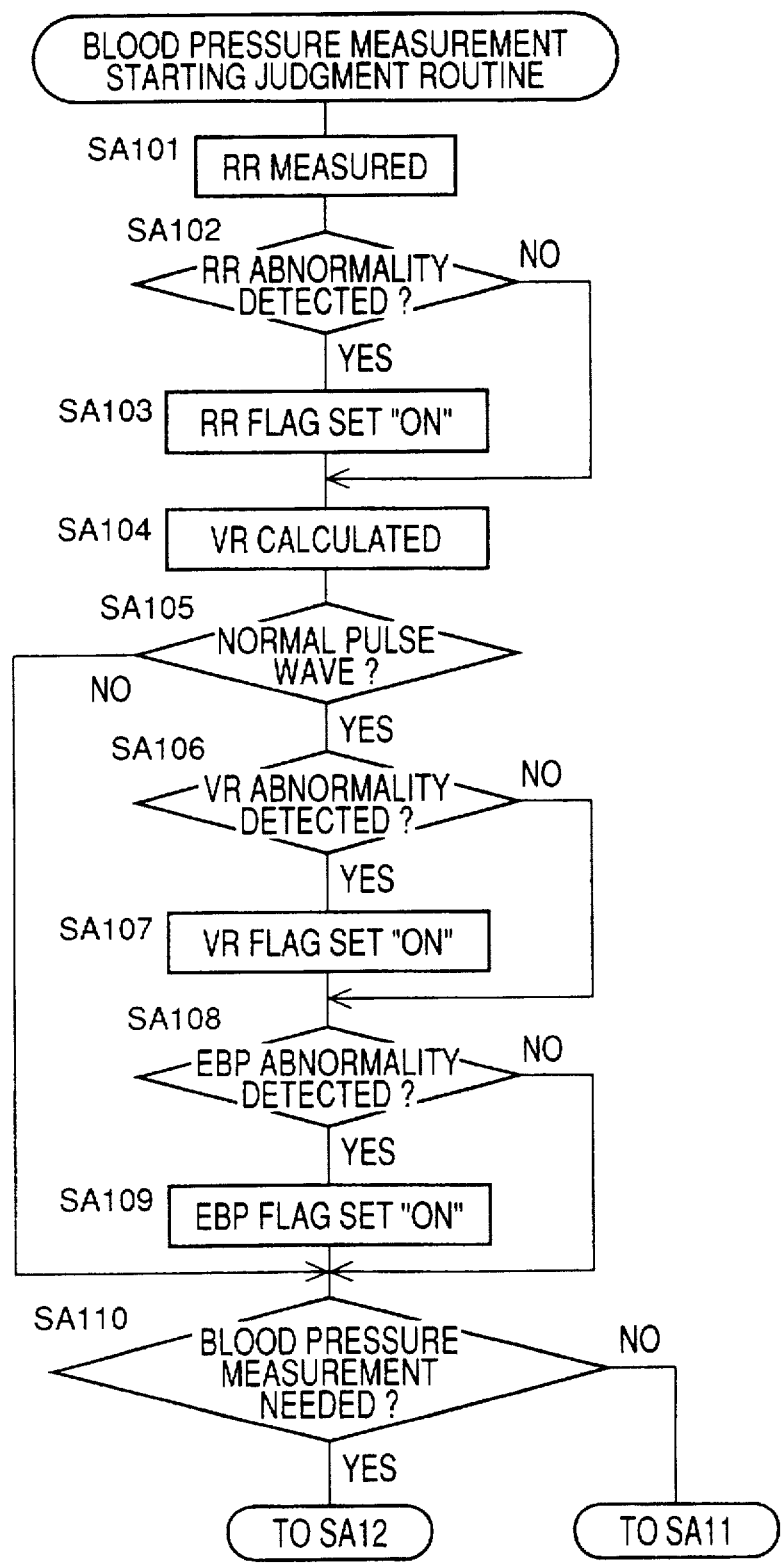
FIG. 7 is a flow chart representing a blood pressure measurement starting judgment routine carried out at Step SA10 of FIG. 6.

Step SA9 is followed by Step SA10 to start a blood pressure measurement of the blood pressure measuring device 70, when the estimated blood pressure value EBP is greater than the first reference value and at least one of the measured pulse period RR and the calculated pulse-wave area VR is greater than a corresponding one of the second and the third reference value, as a result of the execution of a blood pressure measurement starting judgment routine shown in FIG. 7. Step SA10 corresponds to the blood-pressure measurement starting means 86.

At Step SA101 of the flow chart of FIG. 7, the CPU 29 measures the pulse period RR from the ECG waveform detected by the ECG waveform detecting device 34. Step SA101 corresponds to the pulse period measuring device 82. Step SA101 is followed by Step SA102 corresponding to the pulse-period-abnormality judging means 88. At Step SA102, the CPU 29 judges whether or not the measured pulse period RR is abnormal. For instance, the CPU 29 judges that the pulse period is abnormal when a state in which the pulse period RR measured at Step SA101 is, by not less than a predetermined value or a predetermined ratio (e.g., ±5%), greater or smaller than a pulse period measured in the prior blood pressure measurement using the cuff 10 continues during a time period corresponding to more than a predetermined number of pulses (e.g., 20 pulses). If a negative judgment is made at Step SA102, the control of the CPU 29 goes to Step SA104. If a positive judgment is made at Step SA102, the control goes to Step SA103 where a RR flag is set "ON" so as to indicate the abnormality of the pulse period RR.

Step SA103 is followed by Step SA104 to calculate the normalized pulse-wave area VR from the photoelectric pulse wave detected by the probe 38. Step SA104 corresponds to the pulse-wave area calculating means 84. Step SA104 is followed by Step SA105 to judge whether or not the photoelectric pulse wave detected from the peripheral portion (i.e., finger) of the subject is normal. At Step SA105, the CPU 29 eliminates an abnormal waveform of the photoelectric pulse wave. In any rate, the CPU 29 eliminates the waveform of the photoelectric pulse wave when an inclination of a base line of the waveform is greater than a predetermined value, or the waveform changes due to a calibration of the present monitor 8. If a negative judgment is made at Step SA105, the control of the CPU 29 goes to Step SA110. On the other hand, if a positive judgement is made at Step SA105, the control of the CPU 29 goes to Step SA106.

At Step SA106 corresponding to the pulse-wave-area-abnormality judging means 89, the CPU 29 judges whether or not the normalized pulse-wave area VR calculated at Step SA104 is abnormal. For instance, the CPU 29 judges the pulse-wave area is abnormal when a state in which the pulse-wave area VR is, by not less than a predetermined value or a predetermined ratio (e.g., ±3%), greater or smaller than a pulse-wave area calculated in the prior blood pressure measurement continues during a time period corresponding to more than a predetermined number of pulses (e.g., 20 pulses). If a negative judgment is made at Step SA106, the control of CPU 29 goes to Step SA108. If a positive judgment is made at Step SA106, the control of the CPU 29 goes to Step SA107 where a VR flag is set "ON" so as to indicate the abnormality of the pulse-wave area VR.

Next, Step SA107 is followed by Step SA108 corresponding to the estimated-blood-pressure-abnormality judging means 87. At Step SA107, the CPU 29 judges whether or not the estimated blood pressure value EBP determined at Step SA9 is abnormal. For instance, the CPU 29 judges that the estimated blood pressure is abnormal when a state in which the estimated blood pressure value EBP is, by not less than a predetermined value or a predetermined ratio (e.g., ±30%), greater or smaller than an actual blood pressure value determined in the prior blood pressure measurement continues during a time period corresponding to more than a predetermined number of pulses (e.g., 20 pulses). If a negative judgment is made at Step SA108, the control of the CPU 29 goes to Step SA110. If a positive judgment is made at Step SA108, the control of the CPU 29 goes to Step SA109 where an EBP flag is set "ON" so as to indicate the abnormality of the estimated blood pressure value.

Step SA109 is followed by Step SA110 to judge whether or not the EBP flag is "ON" and at least one of the RR flag and the VR flag is "ON". If a negative judgment is made at Step SA110, the control of the CPU 29 goes to Step SA11. At the Step SA 11, the CPU 29 judges whether or not a predetermined period (e.g., 15 to 20 minutes), that is, a calibration period, has passed after the prior blood pressure measurement. If a negative judgment is made at Step SA11, the control of the CPU 29 goes back to Step SA7 and the following steps so as to carry out the blood pressure monitor routine, that is, determine an estimated blood pressure value EBP for each pulse, and timewise display, on the display device 32, the trend graph of the determined estimated blood pressures EBP. On the other hand, if a positive judgment is made at Step SA11, the control of the CPU 29 goes back to Step SA2 and the following steps so as to determine a new blood pressure-pulse wave propagation information relationship between blood pressure and pulse-wave propagation information.

Meanwhile, if a positive judgment is made at Step SA110, the control of the CPU 29 goes to Step SA12 shown in FIG.

6. At Step SA12, the CPU 29 displays the estimated-blood-pressure abnormality on the display device 32. Then, the control of the CPU 29 goes back to Step SA2 to start a blood pressure measurement using the cuff 10 so as to determine a new blood pressure-pulse wave propagation information relationship between blood pressure and pulse-wave propagation information.

In the above described embodiment, the blood pressure measurement of the blood pressure measuring device 70 is started by the blood pressure measurement starting means 86 (Steps SA101 to SA110), when the amount of change of the estimated blood pressure value EBP determined by the estimated blood pressure determining means 78 (Step SA9) is greater than the first reference value and at least one of the amount of change of the pulse period RR measured by the pulse period measuring device 82 (Step SA101) and the amount of change of the pulse-wave area VR calculated by the pulse-wave area calculating means 84 (Step SA104) is greater than a corresponding one of the second and third reference values. Thus, the BP monitor apparatus can employ as small as possible reference values for finding abnormalities, and can identify, without any delay, an unexpected blood pressure change and find an abnormality of the blood pressure. Thus, the reliability of the blood pressure monitor 8 improves, in comparison with a conventional BP monitor apparatus which starts a blood pressure measurement of a blood pressure measuring device, based on only the abnormality of an estimated blood pressure.

In the above described embodiment, the pulse-wave area calculating means 84 (Step SA104) calculates the normalized pulse-wave area VR, by normalizing the area S defined by each pulse of the photoelectric pulse wave, based on the period W and the amplitude L of the waveform of the pulse of the photoelectric pulse wave. Accordingly, the BP monitor apparatus 8 can obtain values VR free from timewise changes or individual differences.

In the above described embodiment, the estimated blood pressure values EBP successively determined by the estimated blood pressure determining means 78 (Step SA9), the pulse period values RR successively measured by the pulse period measuring device 82 and the pulse-wave area values VR successively calculated by the pulse-wave area calculating means 84 are concurrently displayed, on the display device 32, as the respective trend graphs. Since the respective values EBP, RR, VR are concurrently displayed, it is possible to ascertain the reason of the start of the blood pressure measurement by the blood pressure measurement starting means 86 and to easily monitor the dynamic condition of the circulatory organ of the subject while the blood pressure measurement of the blood pressure measuring device 70 is not carried out.

Next, there will be described another embodiment according to the present invention. Hereinafter, the same parts as those of the prior embodiment will be denoted by the same reference numerals and the description thereof is omitted.

Figure 8:
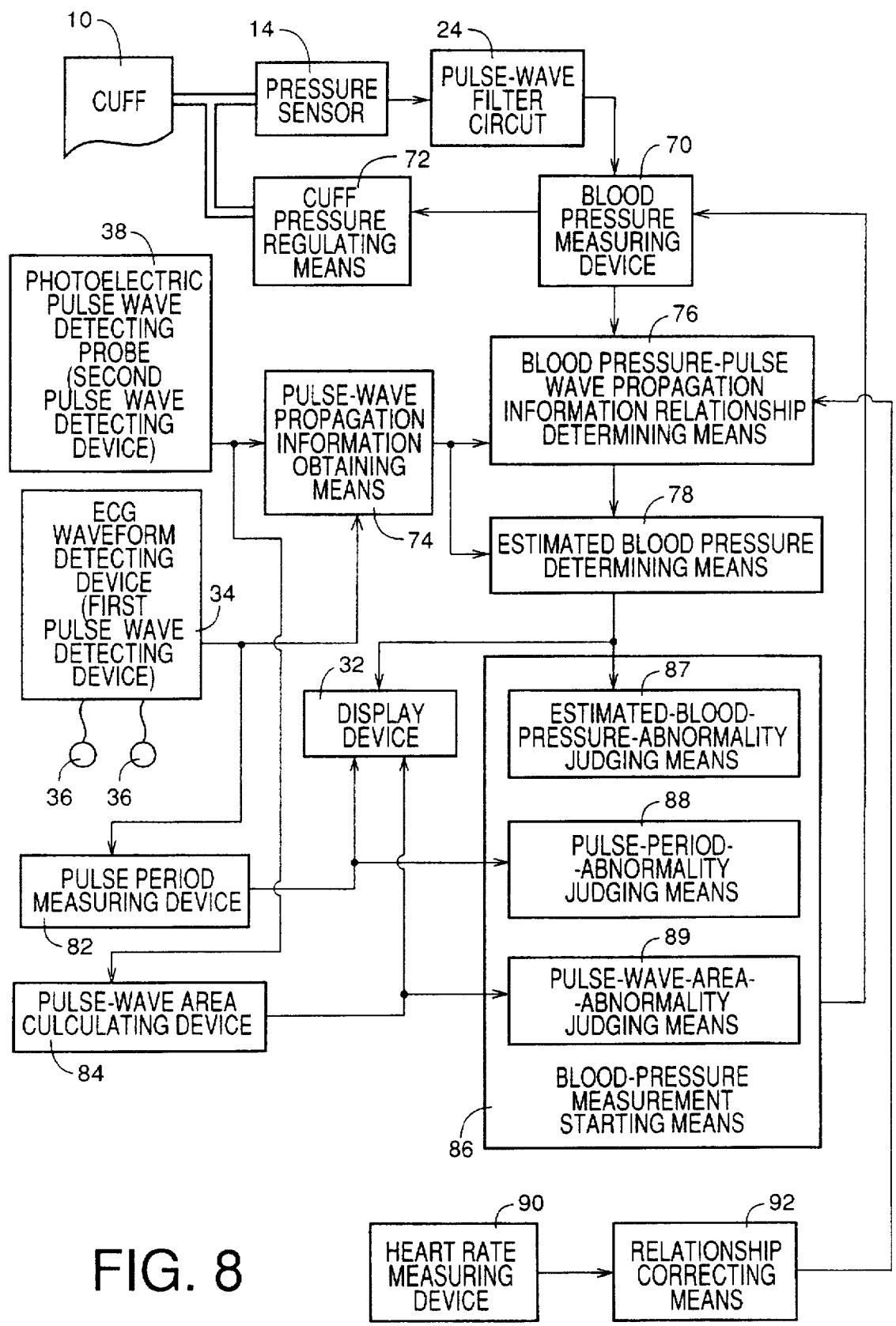
FIG. 8 is a block diagram for explaining essential functions of an electronic control device of a blood pressure monitor apparatus according to another embodiment of the invention.

FIG. 8 is a block diagram for explaining essential functions of an electronic control device 28 of a BP monitor apparatus to which the second embodiment is applied and which has the same hardware construction as that of the prior embodiment shown in FIG. 1. The electronic control device 28 shown in FIG. 8 is different from the electronic control device 28 shown in FIG. 2 in that the former device 28 additionally includes a heart rate measuring device 90 and a relationship correcting means 92.

The heart rate measuring device 90 calculates a heart rate HR (1/min) of a living subject, based on a pulse period RR (sec) measured by the pulse-period measuring device 82, according to a predetermined relationship (e.g., HR=60/RR) pre-stored in a ROM 31.

Figure 9:
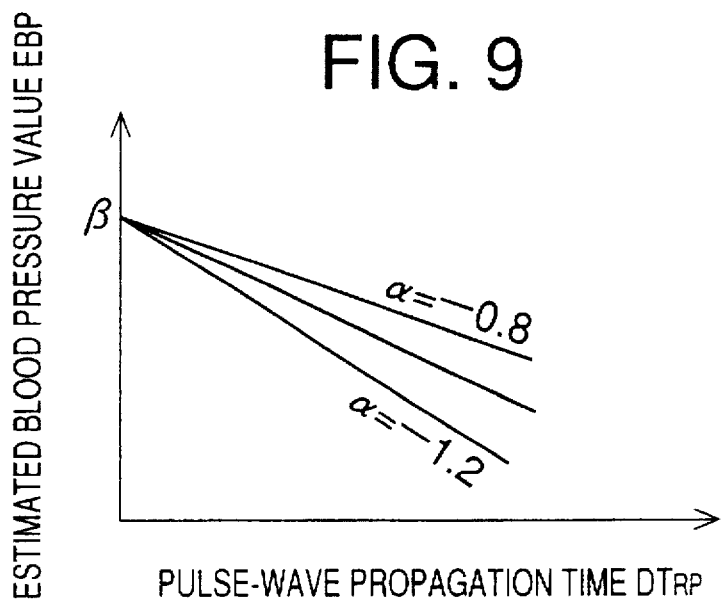
FIG. 9 is a view for illustrating changes of a coefficient for a pulse-wave propagation time $DT_{RP}$ in the relationship between estimated blood pressure EBP and pulse-wave propagation time $DT_{RP}$.

The relationship correcting means 92 corrects the relationship (the expression (2) or (3)) determined by the blood pressure-pulse wave propagation information relationship determining means 76, based on the heart rate HR of the subject. For instance, when the relationship represented by the expression (2) (EBP=$\alpha$DT$_{RP}$+$\beta$) between estimated blood pressure EBP and pulse-wave propagation time DT$_{RP}$ is employed, the relationship correcting means 92 corrects the expression (2) by decreasing an absolute value of the coefficient $\alpha$ (negative value) for the pulse-wave propagation time DT$_{RP}$ in the expression (2), with the increasing of the heart rate HR. As shown in FIG. 9, when the heart rate HR is increased, the relationship correcting means 92 corrects the relationship so that the estimated blood pressure value EBP increases, because, when the absolute value of the coefficient $\alpha$ for the pulse-wave propagation time DT$_{RP}$ is decreased, the slope of the straight line representative of the relationship or expression (2) is decreased and the estimated blood pressure value EBP for the same pulse-wave propagation time value DT$_{RP}$ is increased.

Figure 10:
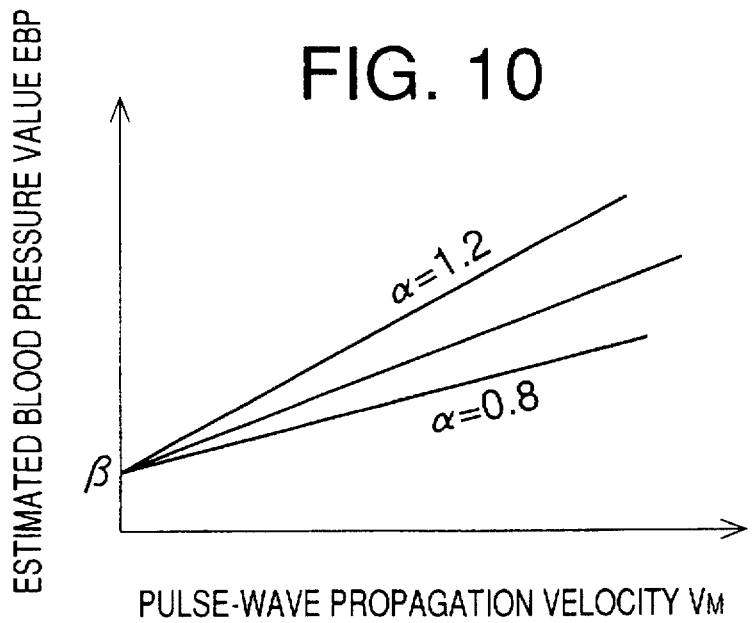
FIG. 10 is a view for illustrating changes of a coefficient for a pulse-wave propagation velocity $V_M$ in the relationship between estimated blood pressure EBP and pulse-wave propagation velocity $V_M$.

Meanwhile, when the relationship represented by the expression (3) (EBP=$\alpha$V$_M$+$\beta$) between estimated blood pressure EBP and pulse-wave propagation velocity V$_M$ is employed, the relationship correcting means 92 corrects the expression (3) by increasing the coefficient $\alpha$ (positive value) for the pulse-wave propagation velocity V$_M$ in the expression (3), with the increasing of the heart rate HR. As shown in FIG. 10, when the heart rate HR is increased, the relationship correcting means 92 corrects the relationship so that the estimated blood pressure value EBP increases, because, when the coefficient $\alpha$ for the pulse-wave propagation velocity V$_M$ is increased, the slope of the straight line representative of the relationship or expression (3) is increased and the estimated blood pressure value EBP for the same pulse-wave propagation velocity value V$_M$ is increased.

Figure 11:
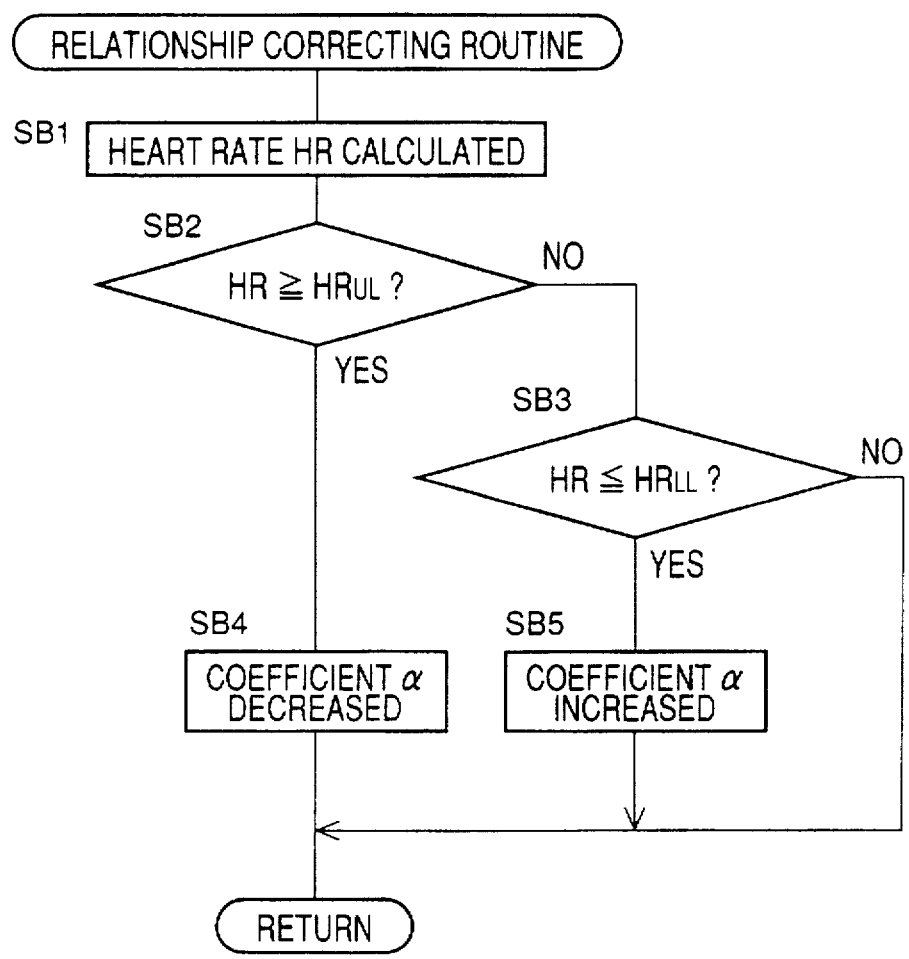
FIG. 11 is a flow chart representing a relationship correcting routine carried out by the electronic control device 28 of the blood pressure monitor apparatus shown in FIG. 8.

FIG. 11 is a flow chart representing a relationship correcting routine which is carried out by the electronic control device 28, independent of the flow charts of FIGS. 6 and 7, in the manner of an interruption handling or a time sharing.

In FIG. 11, at Step SB1, the CPU 29 calculates a heart rate HR of the subject based on the pulse period RR measured at Step SA101 of FIG. 7. Step SB1 corresponds to the heart rate measuring device 90. Step SB1 is followed by Step SB2 to judge whether or not the heart rate HR is greater than a predetermined upper limit value HR$_{UL}$. If a negative judgement is made at Step SB2, the control of the CPU 29 goes to Step SB3 to judge whether or not the pulse rate HR is smaller than a predetermined lower limit value HR$_{LL}$. Those limit values HR$_{UL}$, HR$_{LL}$ are predetermined based on a heart rate HR which is obtained when the blood pressure-pulse wave propagation information relationship is determined by the blood pressure-pulse wave propagation information relationship determined means 76 in the prior blood pressure measurement of the blood pressure measuring device 70 is employed. Preferably, the upper and lower limit values, HR$_{UL}$, HR$_{LL}$, are respectively set at 120% and 80% values of an average value of the ten heart rate values HR calculated for the ten pulses obtained in the prior blood pressure measurement. The upper and lower limit values are, in advance, experimentally set at values suitable for correcting the relationship (the expression (2) or (3)) so as to maintain the accuracy of the estimated blood pressure values EBP. There is known a phenomenon that, when the blood pressure BP of the subject changes, the pulse-wave propagation information (DT, V$_M$) does not change, but the heart rate HR changes.

If a positive judgment is made at Step SB2, the control of the CPU 29 goes to Step SB4. At Step SB4, in the case where the relationship represented by the expression (2) (EBP= $\alpha DT_{RP}+\beta$) between estimated blood pressure EBP and pulse-wave propagation time $DT_{RP}$ is employed, the CPU 29 decreases the absolute value of the coefficient $\alpha$ (negative value) for the pulse-wave propagation time $DT_{RP}$ in the expression (2). For example, the coefficient $\alpha$ is changed from −1.2 to −0.8. In the case where the relationship represented by the expression (3) (EBP=$\alpha V_M+\beta$) between estimated blood pressure EBP and pulse-wave propagation velocity $V_M$ is employed, the CPU 29 increases the coefficient $\alpha$ (positive value) for the pulse-wave propagation velocity $V_M$ in the expression (3). For example, the coefficient $\alpha$ is changed from 0.8 to 1.2.

If a positive judgment is made at Step SB3, the control of the CPU 29 goes to Step SB5. At Step SB5, in the case where the relationship represented by the expression (2) (EBP= $\alpha DT_{RP}+\beta$) between estimated blood pressure EBP and pulse-wave propagation time $DT_{RP}$ is employed, the CPU 29 increases the absolute value of the coefficient $\alpha$ (negative value) for the pulse-wave propagation time $DT_{RP}$ in the expression (2). For example, the coefficient $\alpha$ is changed from −0.8 to −1.2. In the case where the relationship represented by the expression (3) (EBP=$\alpha V_M+\beta$) between estimated blood pressure EBP and pulse-wave propagation velocity $V_M$ is employed, the CPU 29 decreases the coefficient $\alpha$ (positive value) for the pulse-wave propagation velocity $V_M$ in the expression (3). For example, the coefficient $\alpha$ is changed from 1.2 to 0.8. Steps SB2 to SB5 correspond to the relationship correcting means 92.

In the above described second embodiment, the relationship correcting means 92 (Steps SB2 to SB5) corrects the predetermined relationship (the expression (2) or (3)) between estimated blood pressure EBP and pulse-wave propagation information (DT or $V_M$), based on the heart rate HR measured by the heart rate measuring device 90 (Step SB1), so that the estimated blood pressure value EBP increases with the increasing of the heart rate HR. Thus, the accuracy of the estimated blood pressure value EBP is increased and accordingly the reliability of the present blood pressure monitor is improved.

More specifically, in the case where the relationship represented by the expression (2) (EBP=$\alpha DT_{RP}+\beta$) between estimated blood pressure EBP and pulse-wave propagation time $DT_{RP}$ is employed, the relationship correcting means 92 corrects the expression (2) by decreasing the absolute value of the coefficient $\alpha$ (negative value) for the pulse-wave propagation time $DT_{RP}$ in the expression (2), with the increasing of the heart rate HR. When the relationship represented by the expression (3) (EBP=$\alpha V_M+\beta$) between estimated blood pressure EBP and pulse-wave propagation velocity $V_M$ is employed, the relationship correcting means 92 corrects the expression (3) by increasing the coefficient $\alpha$ (positive value) for the pulse-wave propagation velocity $V_M$ in the expression (3), with the increasing of the heart rate HR. In short, the relationship correcting means 92 corrects the relationship (the expression (2) or (3)) so that the estimated blood pressure value EBP increases, with the increasing of the heart rate HR, whereby the accuracy of the estimated blood pressure and the reliability of the blood pressure monitor is raised.

Figure 12:
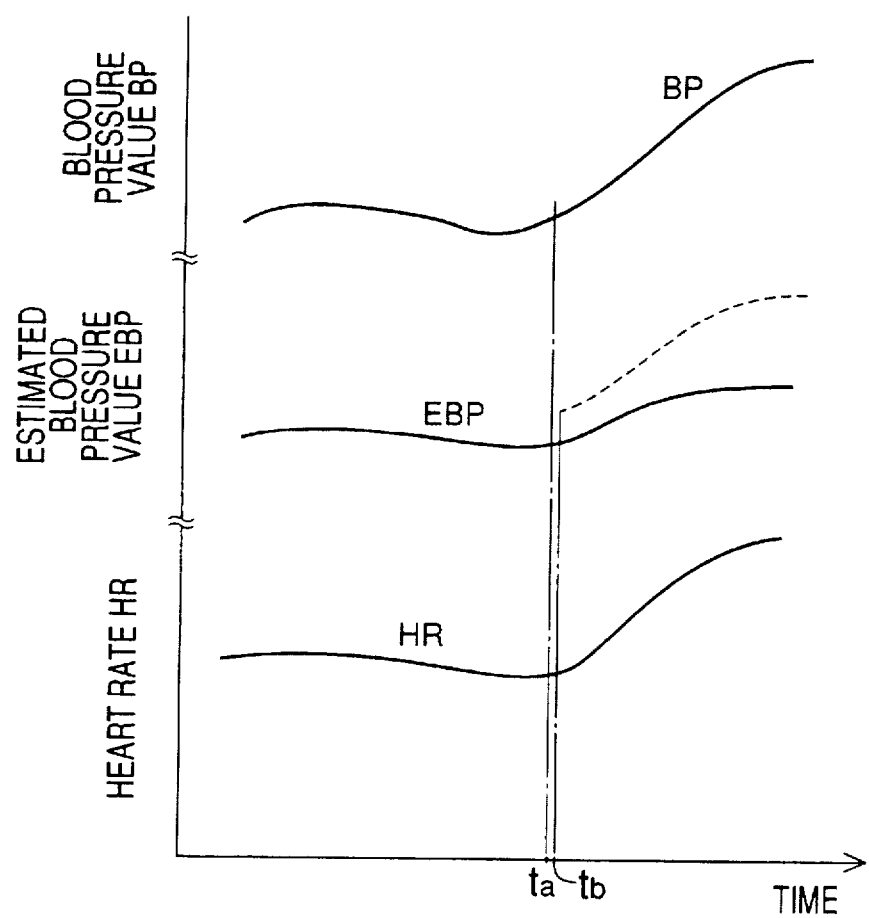
FIG. 12 is a time chart representing the operation of the electronic control device 28 of the blood pressure monitor apparatus shown in FIG. 8.

FIG. 12 shows respective trend graphs of actual blood pressure values BP, the estimated blood pressure values EBP and the pulse rate values HR. In FIG. 12, it is recognized that, after a time point $t_a$, the heart rate HR increases at the same rate as that of the increasing of the blood pressure BP, but the estimated blood pressure EBP does not increase at the same rate as that of the increasing of the blood pressure BP of the subject. When the relationship is corrected at a time point $t_b$, the estimated blood pressure values EBP are determined so as to be greater than the blood pressure values BP by just small amounts. To this end, the relationship correcting means 92 corrects the coefficient $\alpha$. Accordingly, the accuracy of judging of a blood-pressure abnormality is improved, whereby the reliability of the blood pressure monitor are raised.

While the present invention has been described in its preferred embodiments by reference to the drawings, it is to be understood that the invention may otherwise be embodied.

While in each of the illustrated embodiments the blood pressure measuring device 70 employs the so-called oscillometric method, it is possible to employ a so-called Korotokoff-sound method which determines, as a systolic and a diastolic blood pressure value, respective cuff pressures at the time of occurrence and disappearance of Korotokoff-sounds.

While in each of the illustrated embodiments the photoelectric pulse wave detecting probe 38 is used as the peripheral pulse wave detecting device, an impedance sensor being set on a finger of a living subject for detecting the change of impedance of the subject, a pressure pulse wave measuring device being adapted to be pressed on a radial artery of a subject for measuring a pressure in the radial artery of the subject, or the like may be used. In short, any pulse wave representative of circulation dynamics of a peripheral body portion of a subject may be detected and utilized.

While in each of the illustrated embodiments the pulse-wave propagation time $DT_{RP}$ or the pulse-wave propagation velocity $V_M$ is calculated, based on the time difference between the predetermined point of the ECG waveform detected by the ECG waveform detecting device 34 and the predetermined point of the waveform of the photoelectric pulse wave detected by the photoelectric pulse wave probe 38, the pulse-wave propagation time $DT_{RP}$ or the pulse-wave propagation velocity $V_M$ may be calculated using a First pulse wave detecting device being set on a carotid artery or a brachial artery of the subject and a second pulse wave detecting device being set on a wrist or a finger of the subject, in place of the ECG waveform detecting device 34 and the photoelectric pulse wave probe 38.

While in each of the illustrated embodiments the photoelectric pulse wave detecting probe 38 is used as the second pulse wave detecting device, it is possible to employ a cuff pulse wave sensor which detects a cuff pulse wave from the cuff 10 being held at a predetermined cuff pressure, a pressure pulse-wave sensor which is adapted to be pressed on a radial artery of a subject and detects a pressure pulse wave from the artery, an impedance pulse-wave sensor which detects, through electrodes, an impedance pulse wave from an arm or an end portion of a finger of a subject, a light-transmission type photoelectric pulse wave sensor which is adapted to be set on a finger of a subject and detects a photoelectric pulse wave from the finger, or the like.

In each of the illustrated embodiments, the pulse-wave propagation velocity $V_M$ is calculated based on the time difference between the R-wave of the ECG waveform and the rising point of the waveform of the photoelectric pulse wave. However, the pulse-wave propagation velocity $V_M$ may be calculated based on a time difference between a Q-wave of the ECG waveform of each pulse and the rising point of the waveform of a corresponding pulse of the photoelectric pulse wave.

In each of the illustrated embodiments, an estimated blood pressure EBP is determined based on the R-wave of the ECG waveform of each pulse or the waveform of each pulse of the photoelectric pulse wave. However, an estimated blood pressure EBP may be determined based on every second pulse, or so on, of the ECG waveform or the photoelectric pulse wave.

In each of the illustrated embodiments, the pulse period RR (SEC) and the heart rate HR (1/min) may be employed in place of each other, because the pulse period RR corresponds to the heart rate HR, one to one (HR=60/RR).

In the above described second embodiment, the blood pressure measurement starting means 86 may be omitted because it is possible to monitor the blood pressure of the subject by just displaying, on the display device 32, the trend graph of the estimated blood pressure values EBP.

It is to be understood that the present invention may be embodied with other changes and modifications that may occur to those skilled in the art without departing from the scope of the invention.

What is claimed is:

1. A blood pressure monitor apparatus comprising:

a blood pressure measuring device which includes a cuff and measures a blood pressure value of a living subject by changing a pressing pressure of said cuff applied to a body portion of the subject;

pulse-wave propagation information obtaining means for obtaining successive sets of actual pulse-wave propagation information;

blood pressure-pulse information relationship determining means for determining a relationship between blood pressure and pulse-wave propagation information, based on a blood pressure value measured by said blood pressure measuring device and a set of pulse-wave propagation information obtained by said pulse-wave propagation information obtaining means;

estimated blood pressure determining means for successively determining an estimated blood pressure value of the subject, based on each of the successive sets of actual pulse-wave propagation information obtained by said pulse wave propagation information obtaining means, according to the relationship between blood pressure and pulse-wave propagation information determined by said blood pressure-pulse wave propagation information relationship determining means;

a pulse period measuring device which successively measures a period of a pulse of the subject;

a peripheral pulse wave detecting device which detects a peripheral pulse wave from a peripheral body portion of the subject;

pulse-wave area calculating means for successively calculating an area defined by a waveform of a pulse of the peripheral pulse wave detected by said peripheral pulse wave detecting device; and blood pressure measurement starting means for starting a blood pressure measurement of said blood pressure measuring device, when an amount of change of the successively estimated blood pressure values is greater than a first reference value and at least one of an amount of change of the successively measured pulse periods and an amount of change of the successively calculated pulse-wave areas is greater than a corresponding one of a second and third reference value.

2. A blood pressure monitor apparatus according to claim 1, wherein said pulse-wave propagation information obtaining means comprises means for calculating, as said each set of pulse-wave propagation information, at least one of a propagation time and a propagation velocity, based on a time difference between a predetermined point of an electrocardiographic waveform and a predetermined point of a waveform of a pressure pulse wave or a volume pulse wave detected from the peripheral body portion of the subject.

3. A blood pressure monitor apparatus according to claim 1, further comprising an electrocardiographic waveform detecting device which includes a plurality of electrodes adapted to be put on a body surface of the subject and detects an electrocardiographic waveform through the electrodes, wherein said pulse period measuring device comprises means for measuring, as said period of pulse, an interval between two successive R-waves of the electrocardiographic waveform.

4. A blood pressure monitor apparatus according to claim 1, wherein said peripheral pulse wave detecting device comprises a photoelectric pulse wave sensor including a light-emitting and a light-receiving element, the light-emitting element emitting, toward a body surface of the subject, a light including a wavelength which can be reflected by hemoglobin present in blood of the subject, the light-receiving element receiving the light scattered by the hemoglobin from the body surface of the subject.

5. A blood pressure monitor apparatus according to claim 1, wherein said pulse-wave area calculating means comprises means for calculating the pulse-wave area which is normalized based on a period and an amplitude of said pulse of the peripheral pulse wave.

6. A blood pressure monitor apparatus according to claim 1, further comprising a display device which concurrently displays respective trend graphs of the estimated blood pressure values successively determined by said estimated blood pressure determining means, the pulse period values successively measured by said pulse period measuring device and the pulse-wave area values successively calculated by said pulse-wave area calculating means.

7. A blood pressure monitor apparatus comprising:

a blood pressure measuring device which includes a cuff and measures a blood pressure value of a living subject by changing a pressing pressure of said cuff applied to a body portion of the subject;

pulse-wave propagation information obtaining means for obtaining successive sets of actual pulse-wave propagation information;

blood pressure-pulse information relationship determining means for determining a relationship between blood pressure and pulse-wave propagation information, based on a blood pressure value measured by said blood pressure measuring device and a set of pulse-wave propagation information obtained by said pulse-wave propagation information obtaining means;

estimated blood pressure determining means for successively determining an estimated blood pressure value of the subject, based on each of the successive sets of actual pulse-wave propagation information obtained by said pulse wave propagation information obtaining means, according to the relationship between blood pressure and pulse-wave propagation information determined by said blood pressure-pulse wave propagation information relationship determining means;

a heart rate measuring device which measures a heart rate of the subject; and relationship correcting means for correcting said relationship between blood pressure and pulse-wave propagation information, based on the heart rate measured by said heart rate measuring device.

8. A blood pressure monitor apparatus according to claim 7, wherein said relationship comprises a relationship between estimated blood pressure (EBP) and pulse-wave propagation time (DT) which is represented by an expression: $EBP=\alpha DT+\beta$, and wherein said relationship correcting means corrects said expression by decreasing an absolute value of the negative coefficient $\alpha$ for the pulse-wave propagation time DT, with the increasing of the heart rate.

9. A blood pressure monitor apparatus according to claim 7, wherein said relationship comprises a relationship between estimated blood pressure (EBP) and pulse-wave propagation velocity ($V_M$) which is represented by an expression: $EBP=\alpha V_M+\beta$, and wherein said relationship correcting means corrects said expression by increasing an absolute value of the positive coefficient $\alpha$ for the pulse-wave propagation velocity $V_M$, with the increasing of the heart rate.

10. A blood pressure monitor apparatus according to claim 9, wherein said pulse-wave propagation information obtaining means comprises means for calculating, as said each set of pulse-wave propagation information, at least one of a propagation time and a propagation velocity, based on a time difference between a predetermined point of an electrocardiographic waveform and a predetermined point of a waveform of a pressure pulse wave or a volume pulse wave detected from a peripheral body portion of the subject.

11. A blood pressure monitor apparatus according to claim 7, further comprising:

a pulse period measuring device which successively measures a period of a pulse of the subject;

a peripheral pulse wave detecting device which detects a peripheral pulse wave from the peripheral body portion of the subject;

pulse-wave area calculating means for successively calculating an area defined by a waveform of a pulse of the peripheral pulse wave detected by said peripheral pulse wave detecting device; and blood pressure measurement starting means for starting a blood pressure measurement of said blood pressure measuring device, when an amount of change of the successively estimated blood pressure values is greater than a first reference value and at least one of an amount of change of the successively measured pulse periods and an amount of change of the successively calculated pulse-wave areas is greater than a corresponding one of a second and a third reference value.

12. A blood pressure monitor apparatus according to claim 11, wherein said peripheral pulse wave detecting device comprises a photoelectric pulse wave sensor including a light-emitting and a light-receiving element, the light-emitting element emitting, toward a body surface of the subject, a light including a wavelength which can be reflected by hemoglobin present in blood of the subject, the light-receiving element receiving the light scattered by the hemoglobin from the body surface of the subject.

13. A blood pressure monitor apparatus according to claim 11, wherein said pulse-wave area calculating means comprises means for calculating the pulse-wave area which is normalized based on a period and an amplitude of said pulse of the peripheral pulse wave.

14. A blood pressure monitor apparatus according to claim 11, further comprising a display device which concurrently displays respective trend graphs of the estimated blood pressure values successively determined by said estimated blood pressure determining means, the pulse period values successively measured by said pulse period measuring device and the pulse-wave area values successively calculated by said pulse-wave area calculating means.

15. A blood pressure monitor apparatus according to claim 11, further comprising an electrocardiographic waveform detecting device which includes a plurality of electrodes adapted to be put on a body surface of the subject and detects an electrocardiographic waveform through the electrodes, wherein said pulse period measuring device comprises means for measuring, as said period of pulse, an interval between two successive R-waves of the electrocardiographic waveform.

* * * * *